United States Patent [19]

Evans

[11] 4,107,181

[45] Aug. 15, 1978

[54] USEFUL PROSTAGLANDIN INTERMEDIATES

[75] Inventor: David A. Evans, Pasadena, Calif.

[73] Assignee: Regent of the University of California, Berkeley, Calif.

[21] Appl. No.: 768,314

[22] Filed: Feb. 14, 1977

Related U.S. Application Data

[60] Continuation of Ser. No. 687,419, May 17, 1976, abandoned, which is a division of Ser. No. 499,287, Aug. 21, 1974, abandoned, which is a continuation-in-part of Ser. No. 349,888, Apr. 10, 1973, abandoned.

[51] Int. Cl.² ............................................. C07D 317/12
[52] U.S. Cl. ...................... 260/340.9 R; 260/294.8 R; 260/297 R; 260/306.7 R; 548/337; 260/346.22; 568/838; 568/807; 260/448.2 B; 560/121; 260/514 D; 260/586 R; 260/607 R; 260/609 R; 560/122
[58] Field of Search ................................. 260/340.9 R

[56] References Cited

PUBLICATIONS

Evans, et al. *Journ. Org. Chem.*, 39(21), pp. 3176–3178 (1974).
Chem. Abstracts 81:151602w.

*Primary Examiner*—Ethel G. Love

[57] ABSTRACT

The novel synthesis of chemical compounds of the structures 1 and 2 is disclosed.

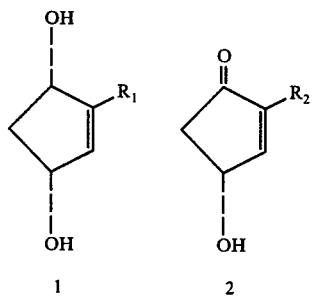

Compounds 1 and 2 are shown to be useful intermediates in prostaglandin synthesis.

1 Claim, No Drawings

USEFUL PROSTAGLANDIN INTERMEDIATES

CROSS REFERENCE TO RELATED APPLICATIONS

This is a continuation, of application Ser. No. 687,419, filed May 17, 1976, now abandoned, which was a division of application Ser. No. 499,287, filed Aug. 21, 1974, now abandoned, which in turn is a continuation-in-part of my co-pending application Ser. No. 349,888 filed Apr. 10, 1973, now abandoned.

BACKGROUND OF THE INVENTION

This invention relates to the synthesis of compounds of formula 1 which are known to be useful for a variety of purposes including use as intermediates in the synthesis of prostaglandins. In the above formula, $R_1$, defined below, includes a member of the group consisting of alkyl, alkenyl, and alkynyl groups of from 2 to 9 carbon atoms which can be substituted by a terminal carboxyl or carboalkoxy group (—COOR') in which the alkyl group (R') is from one to 6 carbon atoms.

In *J. Am. Chem. Soc.* 95:5, Mar. 7, 1973, pp 1676-7 there is described a synthesis of prostaglandin $E_1$ in which 2(6-carboethoxyhexyl)-4-(2-hydroxy)-2-cyclopenten-1-one (i.e., formula 2 where $R_1$ is the 6-carboethoxyhexyl group) is used as an intermediate.

STATEMENT OF THE INVENTION

The first section of this invention relates to the stereoselective synthesis of 1-substituted 1-cyclopentene-cis-3,5-diols (1) where $R_1$ in the formula includes a member of the group consisting of alkyl, alkenyl and alkynyl groups of from 2 to 9 carbon atoms which can be substituted by a terminal 1,3-dioxacycyclopentyl, a carboxyl, or a carboalkoxy group (—COOR') in which the alkyl group (R') is from one to 6 carbon atoms.

The compounds of general structure 1 can be prepared from the hydroxy sulfoxides 6 and 7 in which R is a hydrocarbon radical of from 1 to 12 carbon atoms such as butyl, hexyl, decyl, phenyl or methyl, or a nitrogen and/or sulfur containing 5 to 6 membered heterocyclic radical such as 2-pyridyl, 2-thiazolinyl or 1-alkyl-2-imidazolyl.

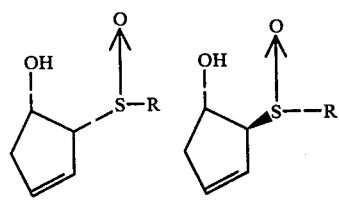

6        7

A general synthetic approach to 6 and 7 is described below for R = phenyl, i.e. Ph. It will be understood that the values for R given above can be used in the scheme.

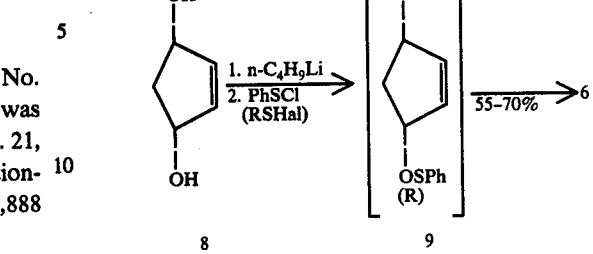

8        9

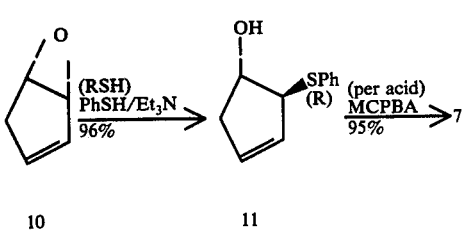

10        11

The processes above are thus a method of producing a compound of the formula

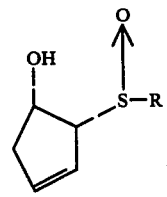

which comprises reacting a compound of the formula:

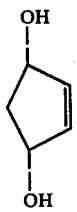

with an alkyllithium and then with RSHal wherein R is a hydrocarbon radical of from 1 to 12 carbon atoms or a nitrogen and/or sulfur containing 5 or 6 membered heterocyclic radical, Hal is a halogen; and allowing the resulting sulfenate ester of the formula:

to rearrange, and also a method of producing a compound of the formula:

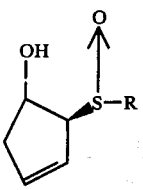

which comprises reacting a compound of the formula:

with RSH in the presence of an organic base wherein R is the same as described immediately above to produce a compound of the formula:

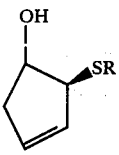

and reacting the latter with a peracid to give compounds of the general structure 7. Both compounds 6 and 7 exist as a diastereoisomeric mixture at the sulfur atom.

EXPERIMENTAL

Both 6 and 7 were prepared as a mixture of sulfoxide diastereoisomers at sulfur. The stereochemical assignments are based on the mode of synthesis.

The cis isomer 6 was prepared by treatment of a 0.25 molar solution of 8 in dry tetrahydrofuran (THF) with one equivalent of n-butyllithium (hexane) at -60° followed by titration with phenylsulfenyl chloride (about 1.25 equivalent) until the persistence of a yellow color. The resulting sulfenate ester 9 was allowed to rearrange to the cis-hydroxy sulfoxide 6 by standing at -20° to 5° C over a 1.5-hour period. The crystalline product 6 was isolated by ether extraction of the aqueous reaction mixture. Sublimation of the product (95°, 0.05 mm Hg) afforded 6, m.p. 102°-112° C, (diastereoisomeric at sulfur) in 55-70% yield, nmr (CDCL$_3$) δ; 7.51 (m, 5H), 6.20 (m, 1H), 5.20 (m, 1H), 3.90 (d, 1H), 3.80 (m, 1H), 2.66 (m, 2H); ir (CDCL$_3$), cm$^{-1}$; 3375, 3040, 1090, 1040, mass spectrum (70 ev) m/e 208 m$^+$.

Anal. Calcd for $C_{11}H_{12}O_2S$: C, 63.45; H, 5.81. Found: C, 63.43; H, 5.86.

The synthesis of the trans-hydroxy sulfoxide 7 (R=Ph) was accomplished in two steps in an overall yield of 91% starting from epoxycyclopentene (10) following the method of M. Korach et al., Org. Syntheses, 42 50 (1962). Treatment of a 2.5 molar solution of 10 in dry benzene at 0° with one equivalent each of thiophenol and triethylamine followed by stirring at 25° C for 4 hours afforded exclusively the trans-hydroxy sulfide as a homogenous liquid (molecular distillation; 90°, 0.05 mm Hg) in 96% yield; nmr (CDCl$_3$) δ; 7.3 (m, 5H), 5.8 (m, 2H), 4.4 (m, 1H), 4.1 (m, 1H), 2.5 (m, 3H); ir (neat) cm$^{-1}$; 3400, 3100, 2950, 1590.

Anal. Calcd for $C_{11}H_{12}OS$: C, 68.74; H, 6.29. Found: C, 68.82; H, 6.34.

Under the same conditions the trans hydroxy sulfide, 12, can be prepared in 77% yield, bp (molecular distillation 80° at .005 mm) m.p. 63°-66°, ir (neat) cm$^{-1}$; 3300, 1460, 1280, 740; nmr (CDCl$_3$) δ: 6.9 (m, 2H), 6.3 (m, 1H), 5.9 (m, 1H), 5.6 (m, 1H), 4.7 (m, 1H), 4.4 (m, 1H), 3.6 (s, 3H), 2.6 (m, 2H); mass spectrum (70 ev) m/e 196 (m$^+$).

Anal. Calcd for $C_9H_{12}N_2OS$: C, 55.09; H, 6.16. Found: C, 54.99; H, 6.06.

The trans hydroxy sulfide 11 (R=Ph) or 12 can also be prepared according to the following general procedure without isolation of the cyclopentadiene epoxide 11.

To a rapidly stirred suspension of 13.25 g (0.125 mol) of anhydrous sodium carbonate in 60 ml. of dry benzene is added 8.3 ml. (0.100 mol) of cyclopentadiene. The solution is cooled to 20° C and 8.4 ml. (0.050 mol) of commercial 40% peracetic acid solution (FMC Corporation) (previously treated with 0.250 g. of sodium acetate to remove sulfuric acid) is added dropwise over a period of 20 min., maintaining the temperature at 20°±5° C. The solution is allowed to warm to room temperature and stirred for 3.5 hr.

The solution is filtered with a Schlenck apparatus under a nitrogen atmosphere and the precipitate washed with 100 ml. of benzene. The benzene solution is cooled with an ice bath and 5.1 ml. (0.05 mol) of thiophenol and 7.0 ml. (0.05 mol) of triethylamine are added rapidly via syringe. The solution is warmed to room temperature and stirred for 18 hours. The solution is extracted with two 50 ml. portions of 5% aqueous sodium hydroxide solution, once with 50 ml. brine and dried with anhydrous granular sodium sulfate. Removal of solvent in vacuo gave 6.1 g. (0.032 mol, 64%) of the sulfide as a light yellow oil. The product was homogeneous by tlc and glpc and was identical in all respects to the material prepared directly from 3,4-epoxy-cyclopentene. The above observed regiospecific cleavage of epoxide 10 with a variety of mercaptide nucleophiles is general.

Oxidation of 11 to the trans-hydroxy sulfoxide 7 was carried out with MCPBA, i.e., m-chloroperbenzoic acid (CH$_2$Cl$_2$, O° C) in 95% yield. Sublimation (90° C, 10$^{-5}$ mm Hg) afforded a nicely crystalline solid, m.p. 96°-113°;

nmr (CDCl$_3$) δ; 7.50 (m, 5H), 6.0C (m, 1H), 5.25 (m, 1H) 4.85 (m, 1H), 3.83 (m, 2H), 2.55 (m, 2H); ir (CHCl$_3$), cm$^{-1}$ 3350, 3075, 3000, 2925, 1580.

Anal. Calcd for $C_{11}H_{12}O_2S$: C, 63.45; H, 5.81. Found: C, 63.31; H, 5.81.

Because both 6 and 7 are hygroscopic; care must be used in handling these compounds in subsequent experiments requiring anhydrous conditions.

Compounds 6 and 7 can be resolved into their optical isomers by one of two procedures. When R is a nitrogen heterocycle such as 12, standard techniques can be employed for the resolution of amines via the use of chiral organic acids such as camphor sulfonic acid. When R is a chiral

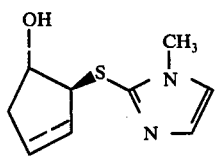

moiety such as menthyl the diastereoisomeric sulfides 6 and 7 can be separated by column chromatography.

The following general procedure is applicable for the transformation of 6 or 7 to the substituted cis-ciols 1.

The method is one of producing a cis-diol compound

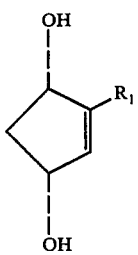

wherein $R_1$ is a member of the group consisting of alkyl, (cis or trans) alkenyl and alkynyl groups of from 2 to 9 carbon atoms which can be substituted by a terminal 1,3-dioxyacyclopentyl, a carboxyl or a carboalkoxy (—COOR') group where R' is an alkyl group of 1 to 6 carbon atoms, which comprises reacting a member of the group consisting of compounds of one of the following formulas or mixtures thereof:

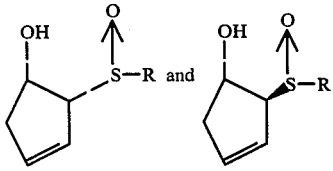

where R is a hydrocarbon radical of from 1 to 12 carbon atoms, or a nitrogen or nitrogen and sulfur containing heterocyclic radical of 5 or 6 members, with lithium dialkyl amine and hexamethylphosphoramide, allowing the reaction to proceed and thereafter adding $R_1Z$ wherein Z is a halogen and recovering said cis diol compound from the reaction mixture.

EXAMPLE 2-(3-methyl-2-butenyl)-cyclopent-2-ene-cis-1,4-diol

To a solution of 1.06 ml. (10.2 mmol) of diethylamine in 15 ml. of dry tetrahydrofuran (THF) at $-60°$ was added 3.7 ml. (9.4 mmol) of n-butyllithium. The solution was stirred at $-10°$ for 15 min. and then cooled to $-40°$. A solution of 0.816 g. (3.92 mmol) of trans 2-phenylsulfinylcyclopent-3-ene-1-ol in 30 ml. of THF was added to this solution, maintaining the temperature at $-40°$. The resulting orange solution was stirred at $-40°$ for 30 min., cooled to $-60°$ and 0.60 ml. (5.09 mmol) of 1-bromo-3-methyl-2-butene was added. The solution was stirred at $-40°$ for 10 min. and the reaction quenched with 2 ml. of saturated ammonium chloride solution and 2 ml. of diethylamine. The solution was allowed to warm to room temperature over 1 hr. and stirred 1.5 hr. at room temperature. The solution was diluted with 200 ml. of diethyl ether and extracted 2X with 50 ml. portions of $H_2O$ and once with 50 ml. of brine. The ether phase was dried with anhydrous sodium sulfate and the solvent removed in vacuo to yield 1.345 g. of brown oil. Chromatography on 90 g. of activity III neutral alumina afforded 470 mg. (2.79 mmol, 71%) of product as a light yellow oil upon elution with 2% methanol in chloroform.

Molecular distillation at 50°, $10^{-5}$ mmHg gave an analytical sample: ir (neat) $cm^{-1}$ 3350, 3000, 2925, 1660, 1460, 1090, 1060, 860; nmr ($CDCl_3$) δ 5.6 (M, 1H), 5.25 (M, 1H), 4.5 (M, 2H), 4.1 (M, 2H), 2.8 (M, 3H), 1.7 (M, 7H).

Anal. Calcd for $C_{10}H_{16}O_2$: C, 71.39; H, 9.59. Found: C, 71.31; H, 9.61.

The following procedure, generally applicable to the above transformation was used to synthesize additional typical representative species of 1.

To a cooled (e.g. $-40°$ to $-60°$) solution of 3.3 mmol of lithium diethylamide (from butyllithium and diethylamine) in 10 ml. of dry THF under nitrogen there is added 1–1.5 ml. of dry hexamethylphosphoramide followed by 1.5 mmol of 6 or 7 in about 4 ml. of THF, with stirring. The deep red solution is stirred for 30 minutes at which time the alkyl halide, $R_1$-Z, (1.6 mmol) is added either as a neat liquor or in a minimum volume of THF. Stirring is continued for an additional 30 minutes at $-40°$, and 2 ml. of a 50% aqueous solution of diethylamine is then added to the reaction mixture. The reaction mixture is allowed to warm to room temperature and stirred for about 2 hours. The product is isolated by the addition of excess water followed by ether extraction of the organic phase with sucessively, 1 N hydrochloric acid and 5% sodium bicarbonate solution, followed by drying over sodium sulfate.

TABLE

| 1-$R_1$-1-cyclopentene-cis-3,5 diols (1) | | | | | |
|---|---|---|---|---|---|
| $R_1Z$ | % Yield, 1 | Mp (bp) ° C | Formula | %C; %H CAlc. | %C; %H found |
| 1-$(CH_2)_5CH_3$ | 50–60 | 75 (5.10$^{-3}$ mm) | $C_{11}H_{20}O_2$ | 71.69; 10.94 | 71.33; 10.78 |
| 1-$(CH_2)_6CH\langle{}^O_O\rangle$ | 54 | 51–52.5 | $C_{14}H_{24}O_4$ | 65.60; 9.94 | 65.76; 9.33 |
| 1-$(CH_2)_6CO_2tBu$ | 45 | 110 (.01 mm) | $C_{16}H_{28}O$ | 67.57; 9.93 | 67.59; 9.77 |
| Br-$CH_2C\equiv C$—$(CH_2)_3CO_2t$-Bu | 33 | 60 (5.10$^{-3}$ mm) | $C_{16}H_{24}O_4$ | 68.55; 8.63 | 68.39; 8.79 |
| $BrCH_2C_6H_5$ | 50 | 95–96.5 | $C_{12}H_{24}O_2$ | 75.76; 7.42 | 75.56; 7.41 |
| $BrCH_2CH=CHC_6H_5$ | 64 | 103–105 | $C_{14}H_{16}O_2$ | 77.75; 7.46 | 77.64; 7.57 |

The representative cis-diols 1 listed in the Table can be purified by chromatography on neutral alumina (Activity III). The cis-diols stereochemistry in 1 is readily assigned by an examination of the 'H-nmr chemical shifts and splitting patterns of the C-4 methylene protons. Thus in 2 ($R_1$ = $CH_2C_6H_5$) the 'H-nmr chemical shifts of the C-4 protons (CDCl₃) are 2.60δ (5-line multiplet) and 1.58δ (triplet of doublets). The corresponding protons in 8 appear at 2.66 and 1.51δ. Reference is made in this respect to F. G. Cocu, G. Wolczunowics, L. Bors, T. Posternak, *Helv. Chim. Acta*, 53, 739 (1970).

Compound 1 can be transformed into prostaglandin precursor 2 by the following route. The oxidation of 1 to the dione 13 is carried out with a variety of reagents such as

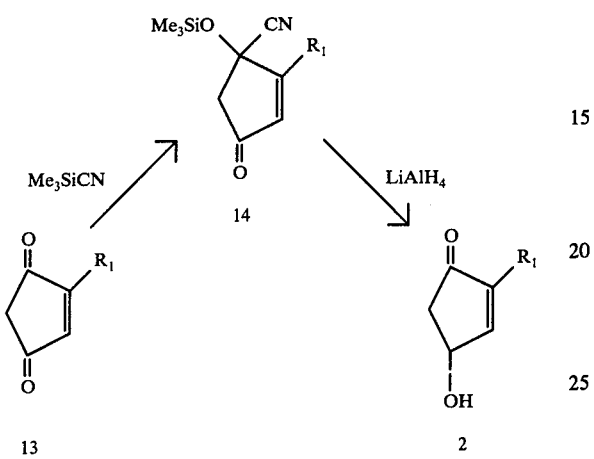

Jones reagent (85% yield). The characteristic ir spectra (neat) of these compounds exhibit a broad carbonyl frequency at 1705 cm⁻¹ and in the nmr spectra, a vinyl 'H-resonance at 0.83 δ (CCl₄).

Selective protection of the ene-dione can be accomplished in the following way. Treatment of 13 with trimethylsilyl cyanide in a variety of nonhydroxylic solvents such as benzene or ether in the presence of a catalytic amount of triphenylphosphine or cyanide ion cleanly affords 14. These compounds are rather difficult to handle and for that reason were not fully characterized. The diagnostic nmr spectra (CCl₄) of these derivatives exhibit vinyl hydrogen absorption at 5.95 δ (1H) and a quartet centered at 2.7 δ (J=18Hz). Compound 14 can be selectively reduced with reducing reagents such as lithium aluminum hydride or sodium borohydride followed by reconstruction of the keto group such as by hydrolysis with aqueous silver fluoride. The method of transforming 13 to 14 follows the method disclosed in *J. Amer. Chem. Soc.*, 95 5822 (1973) and *Chem. Commun.* 55 (1973). The transformation of hydroxyl-protected derivatives of 2 to prostaglandins and prostaglandin analogs of the E-type is completed according to procedures described in the literature, for example E. J. Corey, D. J. Beames, *J. Amer. Chem. Soc.*, 94, 7210 (1972); F. S. Alverez, D. Wren, A. Price, *ibid.*, 94, 7823 (1972); A. F. Kluge, K. G. Untch, J. H. Fried, *ibid.*, 94, 7827 (1972); C. H. Sih, J. B. Heather, G. P. Peruzzotti, P. Price, R. Sood, L. H. Lee, *ibid.*, 95, 1676 (1973) and cited references.

The derivatives 2 possessing the terminal 1,3-dioxacyclopentyl group can be transformed into the corresponding carboxyl compounds by known methods, after protecting hydroxyl group. The resulting carboxyl terminated compounds can then be transformed into prostaglandins as above noted.

A second use of intermediate 1 in prostaglandin synthesis is shown schematically below. Compound species of 1 (below) can be oxidized with reagents such as:

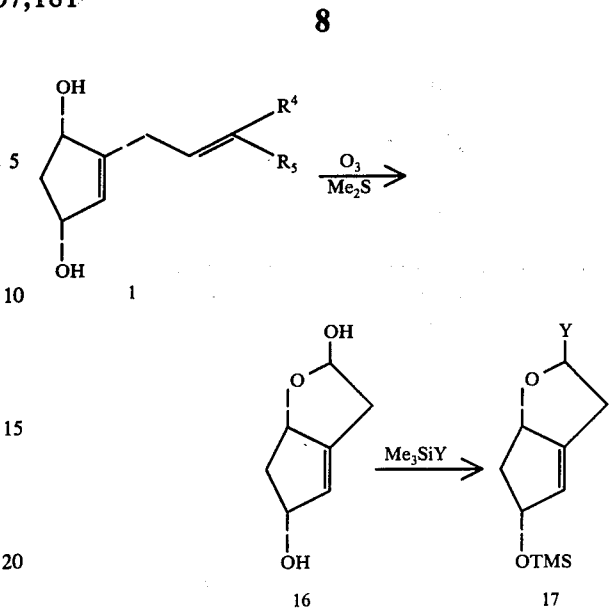

where $R_4$ and $R_5$ are each hydrogen, alkyl or aryl groups preferably hydrogen, alkyl of from 1 to 12 carbons and aryl of from 6 to 12 carbon atoms such as methyl, ethyl, propyl, phenyl and and the like with ozone to the lactol 16 which can be protected with two equivalents of trimethylsilyl methyl sulfide in solvents such as acetonitrile to give compound 17 (Y=SCH₃). Intermediate 17 and similar derivatives such as those where Y=SR₂ or OR₂ where R₂ is a hydrocarbon radical of from 1 to 9 carbons such as alkyl are useful intermediates in prostaglandin synthesis. For example, employing standard organoboron chemistry 17 can be transformed to either 18 or 19 by the sequence of reactions illustrated below. The important concept here involves the hydroboration and subsequent transformation of

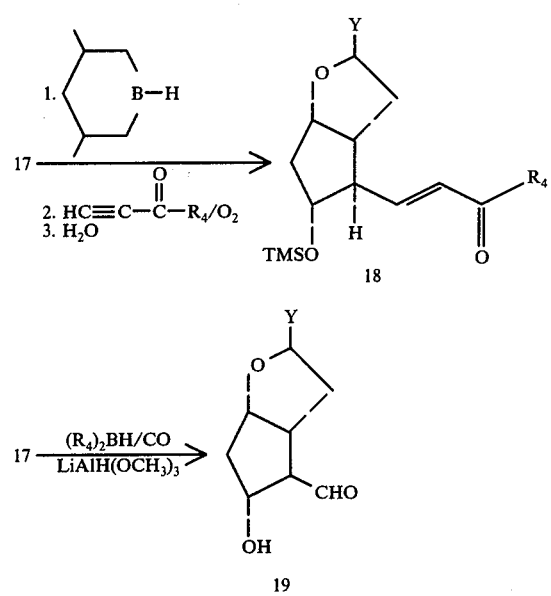

compound 17 to either 18 or 19 by the steps shown above wherein $R_4$ is as defined above.

The reaction 17 - 18 follows that as described in *J. Amer. Chem. Soc.* 92 3503. Thus the borane and (17) can be reacted and the reaction product then reacted with the acylacetylene during aeration.

The reaction 17 – 19 can be carried out in accordance with the disclosure of *Accounts Chem. Res.* 2, 65. Thus 17 (R=C$_6$H$_5$) can be hydroborated in the usual manner at atmospheric pressure and then subjected to gaseous carbon monoxide under agitation as long as absorption continues.

The transformation of both 18 and 19 to F-prostaglandins is disclosed in *J. Amer. Chem. Soc.* 93, 1491.

I claim:

1. A compound of the formula:

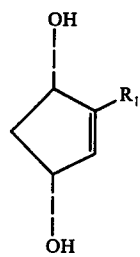

wherein R$_1$ is a member of the group consisting of alkyl, (cis or trans) alkenyl and alkynyl groups of from 2 to 9 carbon atoms substituted by a terminal 1,3-dioxacyclopentyl group.

* * * * *

UNITED STATES PATENT AND TRADEMARK OFFICE
CERTIFICATE OF CORRECTION

PATENT NO. : 4,107,181
DATED : August 15, 1978
INVENTOR(S) : David A. Evans

It is certified that error appears in the above-identified patent and that said Letters Patent are hereby corrected as shown below:

Column 2, Abstract, Formula 2 should appear as follows instead of that which is indicated in the patent:

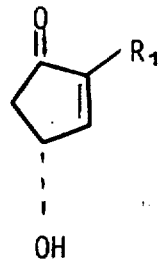

Column 4, line 53: "6.0C" should read -- 6.00 --.
Column 5-6, line 7, table: "$C_{16}H_{28}O$" should read -- $C_{16}H_{28}O_4$ --.
Column 5-6, line 9, table: "$C_{12}H_{24}O_2$" should read -- $C_{12}H_{14}O_2$ --.
Column 7, line 32: "0.83" should read --7.83 --.

Signed and Sealed this

Twenty-seventh Day of March 1979

[SEAL]

Attest:

RUTH C. MASON
Attesting Officer

DONALD W. BANNER
Commissioner of Patents and Trademarks